Figure 1:
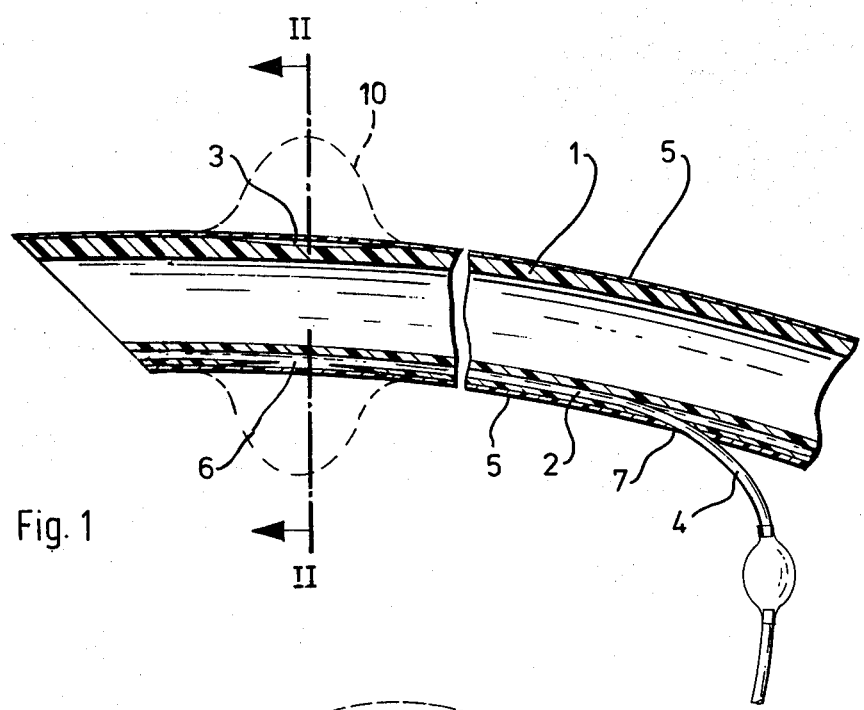

United States Patent [19]

Rüsch

[11] 4,265,848
[45] May 5, 1981

[54] METHOD FOR THE PRODUCTION OF A MEDICAL INSTRUMENT

[75] Inventor: Heinz Rüsch, Waiblingen, Fed. Rep. of Germany

[73] Assignee: Willy Rusch GmbH & Co. KG, Fed. Rep. of Germany

[21] Appl. No.: 67,173

[22] Filed: Aug. 16, 1979

[30] Foreign Application Priority Data

Aug. 30, 1978 [DE] Fed. Rep. of Germany ....... 2837813

[51] Int. Cl.³ .......................................... B29H 21/04
[52] U.S. Cl. .................................. 264/130; 128/349 R; 128/349 B; 128/349 BV; 264/173; 264/264
[58] Field of Search ....................... 264/130, 173, 264; 128/349 R, 349 B, 349 BV

[56] References Cited

U.S. PATENT DOCUMENTS

| | | | |
|---|---|---|---|
| 3,304,353 | 2/1967 | Harautuneian | 264/130 |
| 3,539,674 | 11/1970 | Dereniuk et al. | 264/130 |
| 3,544,668 | 12/1970 | Dereniuk | 264/264 |

FOREIGN PATENT DOCUMENTS

| | | |
|---|---|---|
| 2016607 | 3/1973 | Fed. Rep. of Germany . |
| 2401549 | 10/1974 | Fed. Rep. of Germany . |
| 2532832 | 2/1976 | Fed. Rep. of Germany . |

*Primary Examiner*—Maurice J. Welsh

[57] ABSTRACT

The invention relates to a method for the production of a medical instrument, in particular a tube or catheter, with a balloon made of an elastomeric and/or thermoplastic material, comprising the steps of providing an inflation line for the balloon on or in one hose section and applying thereafter the cuff-shaped balloon with its two ends closely fitting and overlapping one outlet of the said inflation line. To render the production economical, a coat (3) of a parting compound is applied to the hose section (1) in the area where the balloon (10) is to be formed, whereafter the hose is sheathed by extrusion with a sheathing coat (5) of a thermoplastic or elastomeric material.

11 Claims, 2 Drawing Figures

METHOD FOR THE PRODUCTION OF A MEDICAL INSTRUMENT

The present invention relates to a method for the production of a medical instrument, in particular a tube or catheter, with a balloon made of an elastomeric and/or thermoplastic material, comprising the steps of providing an inflation line for the balloon on or in one hose section and applying thereafter the balloon with its two ends closely fitting and overlapping one outlet of the said inflation line.

Certain known methods for the production of a medical instrument equipped with a balloon consist in that initially a hose or hose section with a lumen extending in its longitudinal direction is produced into which an inflation line consisting of a thin hose is inserted which in turn has its end connected to a device for inflating or deflating the balloon, such as a syringe. Or else one produces, for instance by extrusion, a hose having two lumens extending along its longitudinal direction, with the second lumen, which serves as the inflation line and which has a very small cross-section being embedded in the hose wall defining the large lumen. If the hose consists of an appropriate material or was produced appropriately, the balloon may then be applied by dipping. To this end, a parting compound is applied to the balloon area, whereafter the hose is dipped until the skin applied by such dipping exhibits the required thickness. However, when the hose section is produced for instance by die-pressing or extruding, the long hose thus produced is cut into shorter sections onto which the balloon forming the cuff is mechanically fitted; tight fastening of the cuff is then achieved either by serving, if the hose section is for instance made of rubber or a similar material, or by heat-sealing or gluing of the balloon ends.

However, both methods for producing medical instruments comprising a balloon, such as tubes and catheters, are extremely complicated because they require numerous operations to be carried out separately.

Now, it is the object of the present invention to provide a production method permitting the low-cost and still reliable production of medical instruments of this type.

According to the invention, this object is achieved in that initially a coat of a parting compound is applied to the hose section in the area of the balloon to be applied and that then the hose is sheathed with a coat of a thermoplastic or elastomeric material which is applied in one single operation by extrusion.

It is a particular advantage of the method of the invention that it permits the very reliable and at the same time low-cost production of tubes, catheters and the like with a single or multiple balloons and that it permits the hose and the sheathing coat to be of different materials. It is of course possible also to make the hose walls and the sheathing coat of the same material, but in many cases it is preferred to employ a combination of two or even more materials to give the medical instruments produced in this manner certain desired properties which hitherto could not be achieved. For instance, it is now possible to make the hose walls and/or the sheathing coat of PVC or its copolymer, with the addition of a plastisizer. Or else, the hose wall and/or the sheathing coat may be made of a polyolefin. Likewise, the combination of PVC with plastisizer and polyurethane, in particular a thermoplastic polyurethane, may be used for the production of both hose walls and sheathing.

This combination offers the advantage that the balloon is free from any plastisizer so that no plastisizer may penetrate from the packaged inflated balloon into the packaging material. Thus, the very expensive protection of the packing from such plastisizer which was hitherto necessary (multi-layer packing) is no longer needed. Further, this method prevents any migration of plastisizer from the balloon into the shaft which would render the latter excessively soft for practical use.

Finally, the hose wall and/or the sheathing coat may also be made of caoutchouc and/or silicone caoutchouc.

In order to permit the determination of the location of the medical instrument in the patient's body, preferred embodiments of the method of the invention use a material for the hose wall and/or the sheathing coat which is opaque to X-rays. Or else, the end of the inflation lumen is closed at the tip of the instrument with a plastic compound opaque to X-rays, or a metal pin is inserted into the tip of the inflation lumen.

Finally, it is also possible to coat the tip area of the instrument with a varnish compound which is opaque to X-rays.

When extruding the sheathing coat upon the hose section, which may initially have any desired length, the thickness of the sheathing coat may be freely selected within very broad limits, depending on the particular requirements. According to a preferred embodiment of the invention, the sheating coat may also be produced by applying to the hose section different successive layers of the same or else of different materials. In this arrangement, the last layer forms the balloon, while the layers previously applied form a sheathing about the hose section.

In certain preferred embodiments of the invention, the surface to be coated, with the exception of the area to which the parting compound has been applied, is treated with a bonding agent or activated in any other manner, for instance by ionizing radiation or by flames, prior to applying the sheathing coat or—in the case of multilayer sheathings—prior to applying a layer of the sheathing coat. This activation may be achieved either by heating the surface areas in question in order to improve the bonding properties or else by the application in any form whatever of a chemical bonding agent, preferably in liquid form. When a bonding agent is used, it is finally also possible to produce the balloon by the fact that no bonding agent is applied in the area where the balloon is to be formed. As a result, no bond will be achieved between the hose section and the sheathing layer in this area, and in many cases it will not even be necessary to use a parting compound in this area.

When the hose including the main lumen and the inflation lumen is produced by extrusion so that the hose is produced and the inflation lumen formed by one single operation, the method of the invention may immediately follow the production of the hose. In this case, a continuous production line may have the hose production immediately followed by a store, in particular a roll store, followed in turn by a marking device for applying the print. This in turn may be followed by devices for applying the parting compound and/or devices for activating the surface of the hose so that the latter will readily bond to the sheathing coat applied thereafter. In this area, means are also provided for opening the inflation lumen from the outside, for instance by cutting, milling or boring, in the area where the balloon is to be subsequently formed.

This device is in turn followed, if necessary via an additional store—by an extruder with crosshead which applies to the hose the sheathing forming also the balloon. However, the method of the invention also lends itself to the processing of hoses purchased as semi-finished product. While the mehtod described first is mainly suited for larger production series, the latter permits the low-cost production of medical instruments with balloon also in medium and small series.

Medical instruments produced in accordance with the invention offer the advantage that the material of the hose section may be selected along criteria different from those used for the selection of the sheathing material, so that optimum properties of the instrument as a whole and especially of the sheathing coat may be achieved, depending on the particular application of the instrument. In particular, the material used for the sheathing coat will be selected on the one hand to be well tolerated by the body and, on the other hand, to give the balloon the desired properties.

Figure 2:
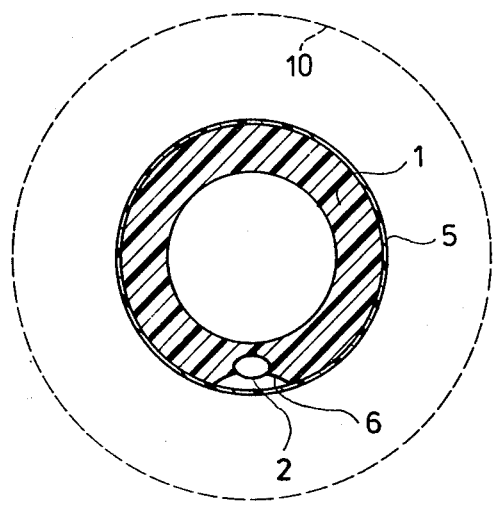

An instrument produced in accordance with the invention, namely a catheter, is shown in the enclosed drawing in which FIG. 1 is a longitudinal section through a catheter and FIG. 2 is a cross-section along line II—II in FIG. 1.

The hose section 1 is produced by die-pressing or extrusion.

During this process, an inflation lumen 2 extending over the whole length of the hose is formed in the wall of the hose section. Following the production of the hose, the desired prints are applied to the hose. In the areas were the hose is to be provided with balloons, a ring of parting compound 3 is applied to the hose. If the inflation lumen 2 is to open outwardly, corresponding openings are milled, cut or provided in any other manner in the corresponding areas. In this operation, the tools are approached to the hose mainly in the tangential direction so as to produce a relatively large cut which will be easily found during the finishing processes.

Thereafter, the hose or hose section 1 is transferred to the crosshead of an extruder for the application of a sheathing coat 5. While passing the crosshead, the hose section is sheathed with a thin coat 5. In order to increase the rigidity of the hose during this operation, an internal pressure may be generated within the hose in a conventional manner. The thin sheathing coat 5 applied bonds firmly to all areas of the hose section 1 where no parting compound 3 has been previously applied or where the surface had not been activated, and forms a balloon 10 in the areas overlying the parting compound 3, and this area also exhibits one opening 6 leading from the inflation lumen 2 to a point below the sheathing coat 5.

In the area opposite the balloon 10, an opening 7 is provided to which an inflation hose 4 is fastened. The opening 6 forming the desired connection between the inflation lumen and the interior of the balloon is provided in the inflation lumen, which was produced in one operation with the production of the hose section, prior to the application of the coat or coats forming the balloon.

The forward end of the catheter adjacent the balloon is heated whereby the edges melt together and the end of the inflation lumen is closed. Instead, however, a PVC tip closing simultaneously the inflation lumen may be fixed by gelling For this purpose, a PVC mixture which is opaque to X-rays may be used. Or else, the inflation lumen may be closed by a plug made of plastic material or metal which is opaque to X-rays and which may be fixed by gluing or else inserted and thereafter fixed by gelling (In the case of the instrument shown in the drawing, this operation was not yet carried out, and the front end of the instrument is still sharp-edged).

I claim:

1. A method for forming a tubular medical instrument, such as a catheter having a balloon cuff of elastic material comprising the steps of forming an elongated hollow hose having an inflation lumen extending along its length and an inflation opening at a selected point on the outer surface, along the length of the hose, applying an annular band of a parting compound to the surface of said hose adjacent said inflation opening and thereafter extruding a continuous cylindrical sheath of elastic material directly about the outer surface of said hose along the length thereof, said sheath simultaneously bonding to the surface of said hose, which is free of said parting compound, and forming an inflatable cuff about said inflation opening.

2. The method according to claim 1, including the step of forming said inflation lumen as an open groove on the outer surface of the hose and enclosing said groove with said sheath.

3. The method according to claim 1, including the step of applying a bonding agent between said hose and said sheath, along the outer surface of said hose, free of said parting agent.

4. The method according to claim 1, wherein said hose is provided with a plurality of inflation openings at preselected spaced intervals therealong, and subsequent to the extrusion of said cylindrical sheath, said hose is severed at selected spaced intervals between said inflation openings to form a plurality of said medical instruments.

5. The method according to claim 4, including the step of enclosing at least one end of said tubular hose subsequent to the extrusion of said sheath thereon.

6. The method according to claims 1, 2 or 3, including the step of subsequently coating the sheath with at least one additional layer of elastic material.

7. The method according to claims 1, 2 or 3, in which the material of said hose and sheath selected from the group consisting of PVC, copolymers of PVC, polyolefin, polyurethane, caoutchouc and silicone caoutchouc.

8. The method according to claim 7, wherein the material of said hose and the material of said sheath are different.

9. The method according to claim 7, including the step of providing a portion of at least one of said hoses and sheaths with material opaque to X-Rays.

10. A method for continuously forming a plurality of medical instruments, such as a catheter, comprising the steps of providing a hollow elongated hose, forming a continuous longitudinal groove on the outer surface of said hose, applying a plurality of annular bands of a parting compound at spaced intervals along said hose, and thereafter extracting a continuous sheath of elastic material about said hose to bond, to the surface thereof, free of said parting compound, said sheath simultaneously, enclosing said groove and forming therewith a continuous inflation lumen and an inflatable balloon about said parting compound, thereafter severing said sheathed hose in intervals between said spaced parting compounds, to form individual sections thereof, and closing the groove of each section at the end nearest to the balloon.

11. A tubular medical instrument, such as a catheter or the like, comprising an elongated hollow hose having a continuous longitudinal groove formed on the outer surface thereof, and a continuous cylindrical sheath of elastic material bonded thereto along a selected section thereof, said sheath being left free of said hose in the remaining section to thereby simultaneously enclose said groove in said selected section to form an inflation lumen, and providing a balloon cuff in the remaining section.

* * * * *